US009412552B2

(12) United States Patent
Aoki et al.

(10) Patent No.: US 9,412,552 B2
(45) Date of Patent: Aug. 9, 2016

(54) MULTI-SOURCE RADIATION GENERATING APPARATUS AND RADIOGRAPHIC IMAGING SYSTEM

(71) Applicant: CANON KABUSHIKI KAISHA, Tokyo (JP)

(72) Inventors: Shuji Aoki, Yokohama (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 108 days.

(21) Appl. No.: 14/337,590

(22) Filed: Jul. 22, 2014

(65) Prior Publication Data

US 2015/0030127 A1     Jan. 29, 2015

(30) Foreign Application Priority Data

Jul. 24, 2013  (JP) ................. 2013-153198

(51) Int. Cl.
| | |
|---|---|
| H01J 35/02 | (2006.01) |
| H01J 35/04 | (2006.01) |
| H01J 35/06 | (2006.01) |
| H01J 35/08 | (2006.01) |
| H01J 35/16 | (2006.01) |
| G01N 23/04 | (2006.01) |

(52) U.S. Cl.
CPC .............. H01J 35/045 (2013.01); H01J 35/06 (2013.01); H01J 35/065 (2013.01); H01J 35/08 (2013.01); H01J 35/16 (2013.01); *G01N 23/04* (2013.01); *H01J 2235/164* (2013.01)

(58) Field of Classification Search
CPC ......... H01J 35/04; H01J 35/045; H01J 35/06; H01J 35/065; H01J 35/14
USPC .......................... 378/122, 124, 134, 137, 138
See application file for complete search history.

(56) References Cited

U.S. PATENT DOCUMENTS

| | | | | | |
|---|---|---|---|---|---|
| 6,215,850 | B1 * | 4/2001 | Blake | ...................... | H05G 1/32 378/101 |
| 6,233,309 | B1 * | 5/2001 | Baptist | ................. | G03B 42/047 378/162 |
| 6,456,691 | B2 * | 9/2002 | Takahashi | .............. | B82Y 10/00 378/122 |
| 6,553,096 | B1 * | 4/2003 | Zhou | .................... | A61B 6/4488 378/122 |
| 6,944,268 | B2 * | 9/2005 | Shimono | ............... | H01J 35/045 378/111 |
| 7,082,182 | B2 * | 7/2006 | Zhou | ...................... | A61B 6/032 378/10 |
| 7,085,351 | B2 * | 8/2006 | Lu | ........................ | A61B 6/4021 315/169.3 |
| 7,120,222 | B2 * | 10/2006 | Hoffman | ................ | A61B 6/032 378/124 |
| 7,245,692 | B2 * | 7/2007 | Lu | .......................... | G01N 23/04 378/122 |
| 7,440,547 | B2 * | 10/2008 | Ishiyama | ............... | A61B 6/032 378/101 |
| 7,496,180 | B1 * | 2/2009 | Subraya | .................. | H01J 35/14 378/137 |

(Continued)

FOREIGN PATENT DOCUMENTS

| | | |
|---|---|---|
| JP | 59-068200 A | 4/1984 |
| JP | 2006-086001 A | 3/2006 |

*Primary Examiner* — Allen C. Ho
(74) *Attorney, Agent, or Firm* — Canon USA Inc. IP Division

(57) ABSTRACT

In a multi-source radiation generating apparatus including a plurality of combinations of a cathode and a target, an extraction electrode is disposed for a plurality of cathodes in common. When a potential of the extraction electrode is constant, potentials for the cathodes are selectively switched between a cutoff potential which is higher than the potential of the extraction electrode and an emission potential which is lower than the potential of the extraction electrode.

8 Claims, 9 Drawing Sheets

(56) References Cited

U.S. PATENT DOCUMENTS

| | | | |
|---|---|---|---|
| 7,505,562 B2 * | 3/2009 | Dinca | G01N 23/201 378/57 |
| 7,529,344 B2 * | 5/2009 | Oreper | H01J 35/045 378/134 |
| 7,606,349 B2 * | 10/2009 | Oreper | G01V 5/005 378/137 |
| 7,627,087 B2 * | 12/2009 | Zou | H01J 1/304 378/122 |
| 7,646,852 B2 * | 1/2010 | Harding | H05G 1/52 378/111 |
| 7,792,241 B2 * | 9/2010 | Wu | H01J 35/045 378/114 |
| 7,801,277 B2 | 9/2010 | Zou et al. | |
| 7,809,114 B2 * | 10/2010 | Zou | H01J 1/3048 378/122 |
| 7,826,594 B2 * | 11/2010 | Zou | H01J 1/30 378/10 |
| 7,826,595 B2 * | 11/2010 | Liu | H01J 35/065 378/122 |
| 7,852,979 B2 * | 12/2010 | Edic | A61B 6/032 378/134 |
| 7,873,146 B2 * | 1/2011 | Okunuki | H01J 35/065 378/122 |
| 7,991,114 B2 * | 8/2011 | Okunuki | A61B 6/032 378/11 |
| 7,991,120 B2 * | 8/2011 | Okunuki | A61B 6/00 378/122 |
| 8,155,273 B2 * | 4/2012 | Eaton | H01J 35/065 378/122 |
| 8,220,993 B2 * | 7/2012 | Takahashi | H01J 35/06 378/207 |
| 8,358,741 B2 * | 1/2013 | Grasruck | H01J 35/045 378/113 |
| 8,374,315 B2 * | 2/2013 | Freudenberger | H01J 35/06 378/134 |
| 8,396,185 B2 * | 3/2013 | Zou | A61B 6/032 378/112 |
| 8,447,013 B2 * | 5/2013 | Sprenger | H01J 35/04 378/122 |
| 8,487,534 B2 * | 7/2013 | Caiafa | H05G 1/32 315/111.31 |
| 8,488,742 B2 * | 7/2013 | Tsujii | A61B 6/4441 378/138 |
| 8,498,380 B2 * | 7/2013 | Behling | H01J 35/04 378/138 |
| 8,699,657 B2 * | 4/2014 | Baeumer | A61B 6/032 250/494.1 |
| 9,058,958 B2 * | 6/2015 | Aoki | H01J 35/04 |
| 9,070,529 B2 * | 6/2015 | Tamura | H01J 35/12 |
| 9,076,627 B2 * | 7/2015 | Yanagisawa | H01J 35/16 |
| 9,159,525 B2 * | 10/2015 | Yamazaki | H01J 35/06 |

* cited by examiner

MULTI-SOURCE RADIATION GENERATING APPARATUS AND RADIOGRAPHIC IMAGING SYSTEM

BACKGROUND OF THE INVENTION

1. Field of the Invention

The present invention relates to a multi-source radiation generating apparatus which is applicable to nondestructive inspection apparatus in a field of medical equipment and a field of industrial equipment and a radiographic imaging system employing the multi-source radiation generating apparatus.

2. Description of the Related Art

In general, an X-ray generating apparatus generates radiation by irradiating target electrodes (targets) with high-energy electrons emitted from electron sources (cathodes). To that end, the cathodes and the targets are disposed in a radiation tube which is maintained in a vacuum state. Japanese Patent Laid-Open No. 59-068200 discloses an X-ray computed tomography (CT) apparatus which generates an X-ray of a pulse shape by applying a pulse voltage to a grid while it is assumed that a voltage between an anode and a cathode is set to substantially constant.

A multi-source radiation generating apparatus including a plurality of target electrodes (targets) which are disposed so as to face corresponding electron sources has been widely used. In a multi-source radiation generating apparatus, emission/non-emission of electrons from the electron sources are individually controlled, and therefore, extraction electrodes are disposed for individual electron sources. Accordingly, the arrangement of the extraction electrodes, the layout of connection lines to the extraction electrodes, and the arrangement of other electronics is complicated.

SUMMARY OF THE INVENTION

Embodiments of the present invention disclose a multi-source radiation generating apparatus capable of individually controlling emission/non-emission of electrons from a plurality of electron sources with a simple configuration. A small radiographic imaging system employing the multi-source radiation generating apparatus is achieved.

As disclosed herein, a radiation generating apparatus comprises a radiation tube, and a driving controller configured to control driving of the radiation tube. The radiation tube includes a plurality of cathodes which emit electrons, a plurality of targets which are disposed so as to correspond to the cathodes and which output radiation in response to the emission of electrons, and an extraction electrode which is disposed between the cathodes and the targets. The driving controller performs switching between a cutoff potential which is higher than a potential of the extraction electrode and an emission potential which is lower than the potential of the extraction electrode so that the cutoff potential and the emission potential are selectively applied to each of the cathodes.

Further features of the present invention will become apparent from the following description of exemplary embodiments with reference to the attached drawings.

DESCRIPTION OF THE EMBODIMENTS

Exemplary embodiments of the present invention will be described hereinafter with reference to the accompanying drawings. Although radiation employed in the exemplary embodiments is an X-ray, the exemplary embodiments are applicable to a neutron ray and a proton beam.

First Exemplary Embodiment

Figure 1:
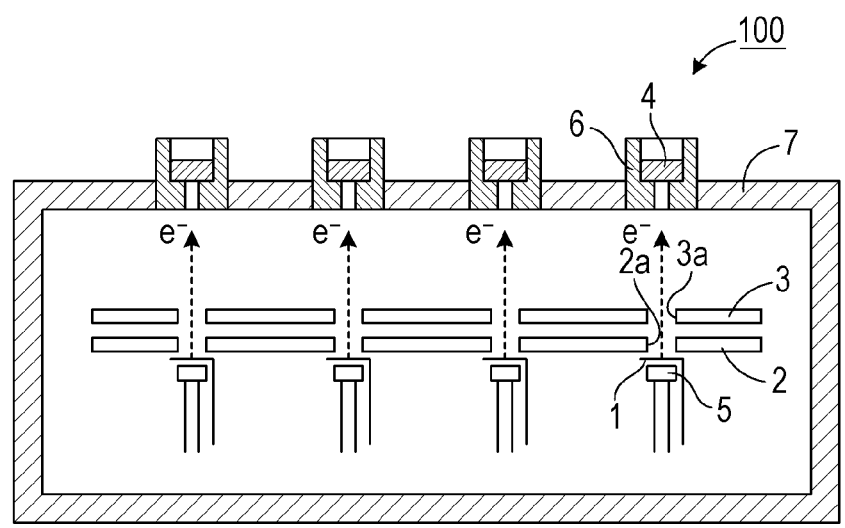
FIG. 1 is a sectional view schematically illustrating a configuration of a radiation tube according to a first exemplary embodiment.

FIG. 1 is a sectional view schematically illustrating a configuration of a radiation tube 100 according to a first exemplary embodiment.

The radiation tube 100 is a multi-source radiation tube including a plurality of combinations of a cathode 1 to produce an electron source which emits electrons and a target (anode) 4 which generates radiation when an electron beam collides against (strikes) the target 4. The radiation tube 100 further includes an extraction electrode 2 which applies an intense electric field used to extract electrons from the cathodes 1 and an intermediate electrode 3 which converges the extracted electrons with an electric field serving as an electron beam. The cathodes 1, the extraction electrode 2, and the intermediate electrode 3 are disposed in a vacuum container 7.

As an electron source, a cold cathode electron source or a hot cathode electron source is applicable. However, in terms of stable extraction of electron beams of large current, a liquid metal impregnated electron source is preferably employed. In this exemplary embodiment, hot cathode electron sources having a simple configuration each of which includes a heater (filament) 5 and the cathode 1 insulated from the heater 5 are used. The extraction electrode 2 and the intermediate electrode 3 may be formed of an electrically-conductive metal, such as molybdenum or the like. The intermediate electrode 3 is disposed between the cathodes 1 and the targets 4, and the extraction electrode 2 is disposed between the cathodes 1 and the intermediate electrode 3.

Although the targets 4 may be formed of a single material which generates radiation by bombardment of electron beams, the targets 4 may be formed by laminating target layers of materials which generate radiation by bombardment of electron beams on a substrate formed by a material which allows the radiation to pass. As constituent material of the substrate, low-atomic-number materials, such as beryllium or diamond, is preferably used. As constituent material of the target layers, heavy metal material having an atomic number of 26 or more is preferably used in terms of efficiency of generation of radiation. Specifically, materials including tungsten, molybdenum, chrome, copper, cobalt, iron, rhodium, or rhenium or an alloy such materials may be used.

The targets 4 are arranged as partitions disposed at intermediate portions of hollow portions included in cylindrical support bases 6 disposed so as to penetrate the vacuum container 7, and face the corresponding cathodes 1. The cylindrical support bases 6 and the targets 4 form part of a wall surface of the vacuum container 7 and contribute maintaining of vacuum tight of the vacuum container 7.

The individual targets 4 are disposed so as to face the cathodes 1 in a one-to-one correspondence. The extraction electrode 2 and the intermediate electrode 3 are disposed for all cathodes 1 in common. The extraction electrode 2 and the intermediate electrode 3 have openings 2a and 3a, respectively, through which electrons emitted from the cathodes 1 pass.

Figure 2:
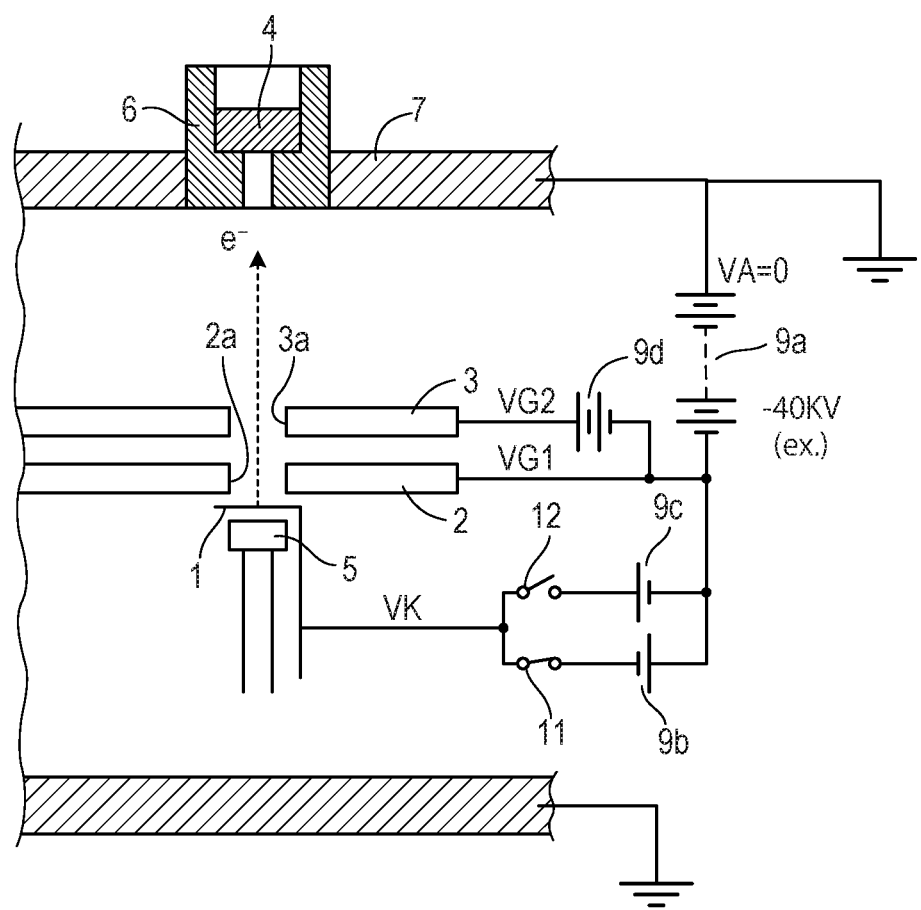
FIG. 2 is a diagram schematically illustrating an exemplary circuit for applying potentials to electrodes included in the radiation tube according to the first exemplary embodiment.
Figure 3:
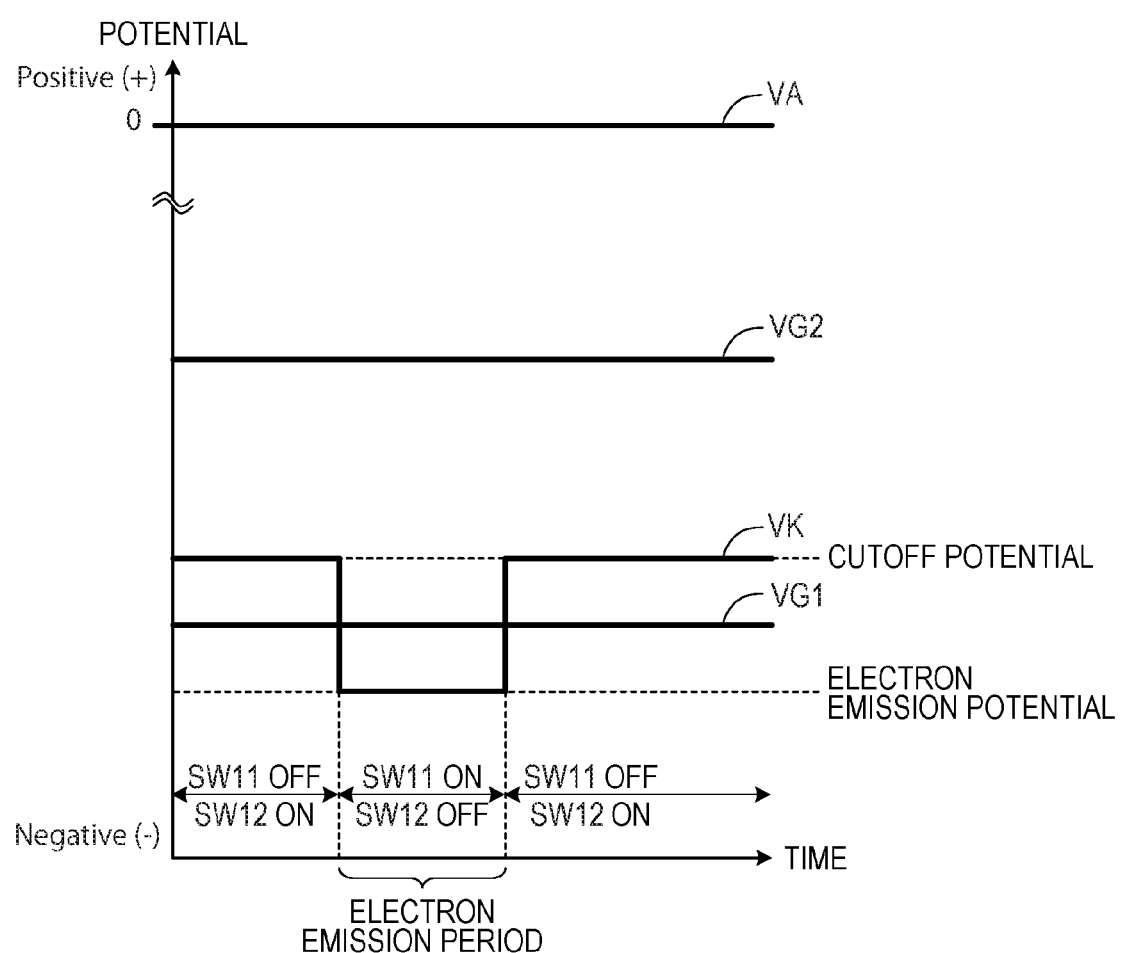
FIG. 3 is a time diagram illustrating the relationship among potentials of the electrodes.

Examples of states of potentials of the radiation tube 100 are illustrated in FIGS. 2 and 3. As illustrated in FIG. 2, the vacuum container 7 and the targets 4 have the same potential (ground potential). A voltage source 9a regulates potential differences between the target 4 and the extraction electrode 2. Voltage sources 9b and 9c are cathode potential regulating units which selectively regulate a potential of the cathodes 1. A voltage source 9d is an intermediate electrode potential regulation unit which regulates a potential of the intermediate electrode 3. The voltage source 9b applies a negative potential (an emission potential) to the cathodes 1 using a potential of the extraction electrode 2 as a reference so that the cathodes 1 emit electrons. Similarly, the voltage source 9c applies a positive potential (a cutoff potential) to the cathodes 1 so as to suppress emission of electrons from the cathodes 1.

As illustrated in FIG. 3, a potential of the targets 4 is denoted by "VA", a potential of the intermediate electrode 3 is denoted by "VG2", a potential of the extraction electrode 2 is denoted by "VG1", and a potential of the cathodes 1 is denoted by "VK". Voltage potentials VA, VG1, and VG2 have substantially constant values. The relationship in an "electron emission period" among the potentials of the cathodes 1, the extraction electrode 2, the intermediate electrode 3, and the targets 4 for collision of accelerated electron beams to the targets 4, is represented by the following expression: VK<VG1<VG2<VA, where VA=0 (ground), is described (or is readable) in FIG. 3. The relationship in a rest period of the electron emission period (or in a electron non-emission period) among the cathodes 1, the extraction electrode 2, the intermediate electrode 3, and the targets 4 for suppressing emission of electron beams from the cathode 1, represented by the following expression: VG1<VK<VG2<VA, where VA=0 (ground), is described (or is readable) in FIG. 3. Specifically, in a state in which the potential VG1 of the extraction electrode 2 is set to be constant, electron emission is suppressed when the potential VK of the cathodes 1 is set as a cutoff potential which is higher than the potential VG1, whereas electron emission is performed when the cathode potential VK is set as an emission potential which is lower than the potential VG1 in the "electron emission period" in FIG. 3.

A potential difference between the cathode potential VK and the extraction electrode potential VG1 is in a range from approximately 50 volts (V) to approximately 500 V. A potential difference between the extraction electrode potential VG1 and the intermediate electrode potential VG2 is in a range from approximately 1 kV to approximately 10 kV. A potential difference between the extraction electrode potential VG1 and the target potential VA is in a range from approximately 10 kV to approximately 150 kV. Specifically, electron beams extracted from the cathodes 1 collide with (or strike) the targets 4 with energy in a range from approximately 10 keV to approximately 150 keV so that radiation is generated.

A switch (SW) 11 is used to connect the voltage source 9b to the cathode 1, and a switch (SW) 12 is used to connect the voltage source 9c to the cathode 1. As illustrated in FIG. 3, the switches 11 and 12 are not simultaneously turned on. The switches 11 (SW11) and 12 (SW12) are selectively controlled such that, at a time when the switch 11 is in an on state (SW11 ON), the switch 12 is in an off state (SW12 OFF); and at a time when the switch 11 is in an off state (SW11 OFF), the switch 12 is in an on state (SW12 ON).

Next, a configuration and operation of the multi-source radiation generating apparatus (hereinafter referred to as a radiation generating apparatus) of this exemplary embodiment will be described.

Figure 4:
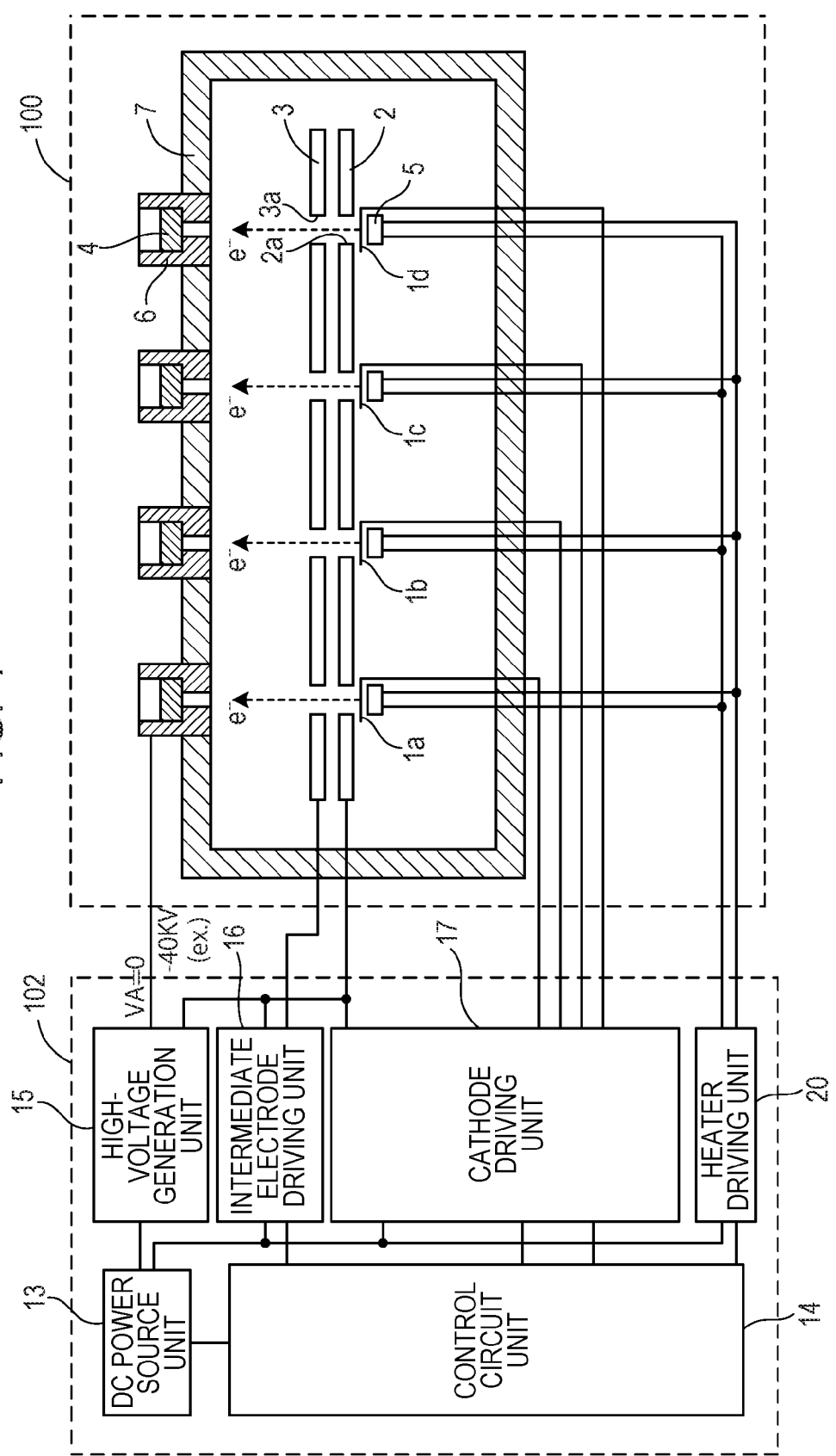
FIG. 4 is a block diagram illustrating a configuration of a multi-source radiation generating apparatus according to the first exemplary embodiment.

As illustrated in FIG. 4, the radiation generating apparatus includes the radiation tube 100 and a driving controller 102 which controls driving of the radiation tube 100. The driving controller 102 includes a direct current (DC) power source unit 13, a control circuit unit 14, and control blocks (including a high-voltage generation unit 15, an intermediate electrode driving unit 16, a cathode driving unit 17, and a heater driving unit 20).

The DC power source unit 13 receives electric power from an external DC power source or an external alternate current (AC) power source and supplies desired DC electric power to the control circuit unit 14 and the control blocks. The control circuit unit 14 outputs control signals to the control blocks in response to a request for outputting radiation externally supplied.

The high-voltage generation unit 15 generates a high voltage of −40 kV and applies the voltage of −40 kV to the extraction electrode 2. The radiation tube 100 is an anode grounded radiation tube in which the targets 4 are grounded (as shown in FIG. 2). The high-voltage generation unit 15 generates an acceleration DC voltage of −40 kV in response to a control signal supplied from the control circuit unit 14.

The intermediate electrode driving unit 16 outputs an intermediate electrode voltage of DC in a range from −10 kV to −30 kV to the intermediate electrodes 3 in response to a control signal supplied from the control circuit unit 14.

Figure 5:
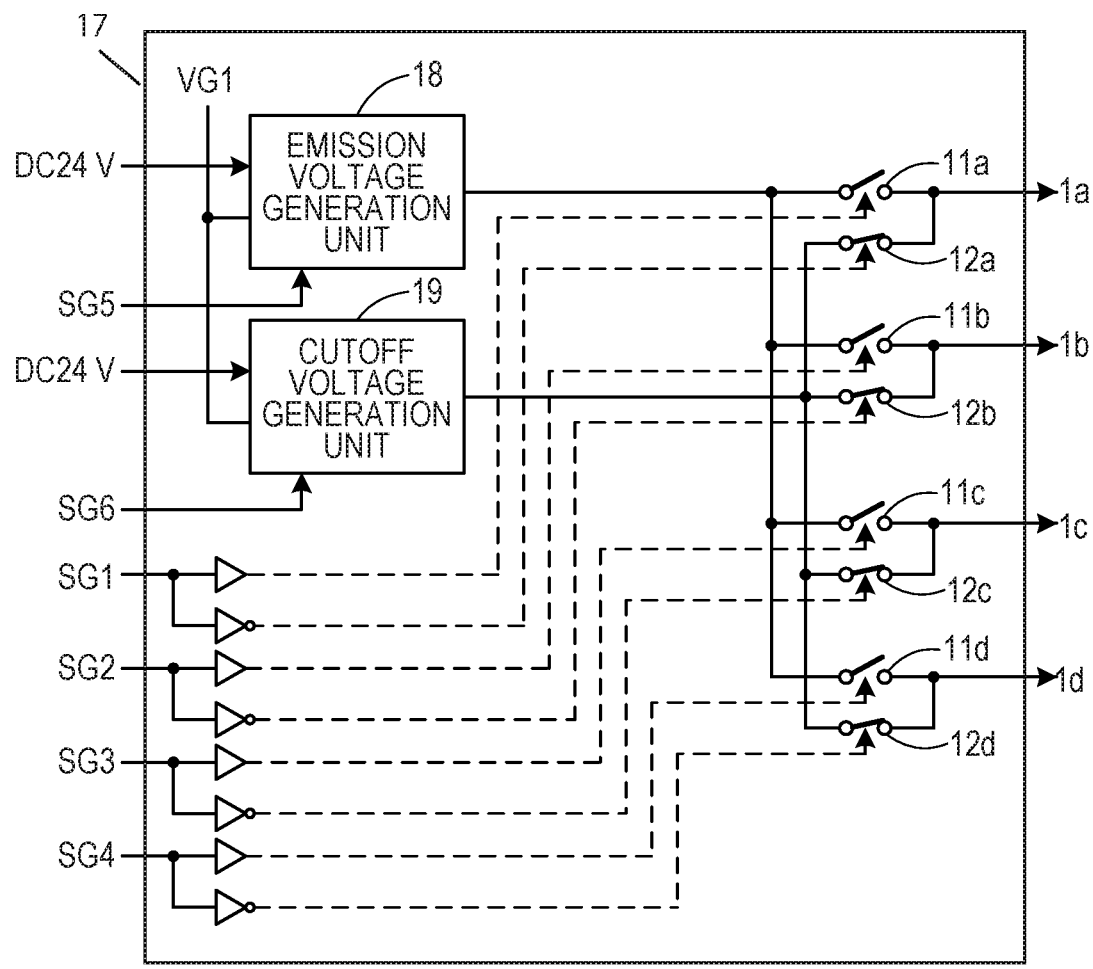
FIG. 5 is a block diagram illustrating a configuration of a cathode driving unit according to the first exemplary embodiment.
Figure 6A:
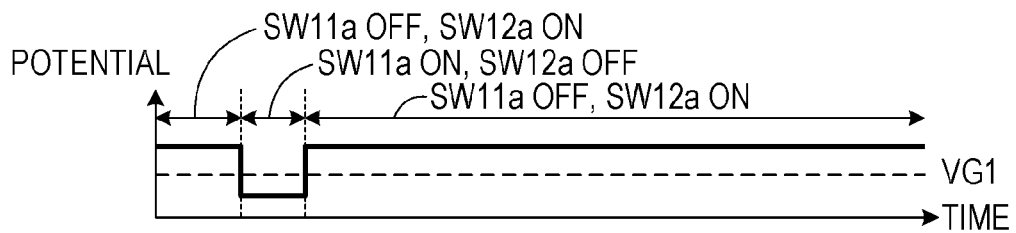
FIGS. 6A, 6B, 6C to 6D are timing charts illustrating timed change of a cathode potential according to the first exemplary embodiment.
Figure 6B:
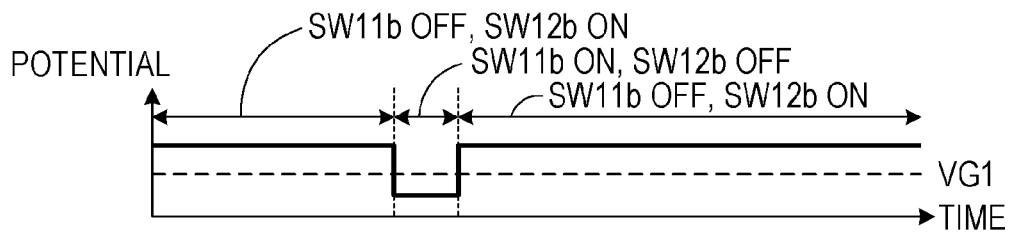
Figure 6C:
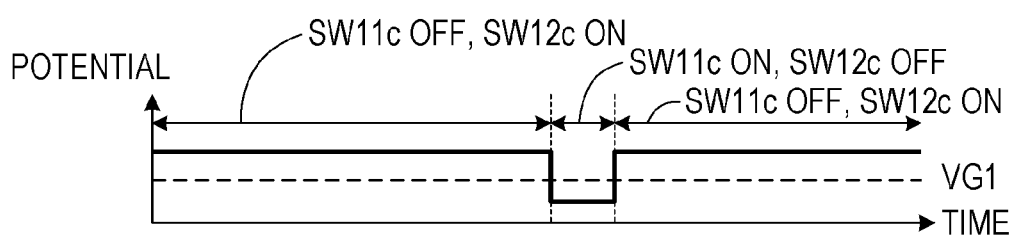
Figure 6D:
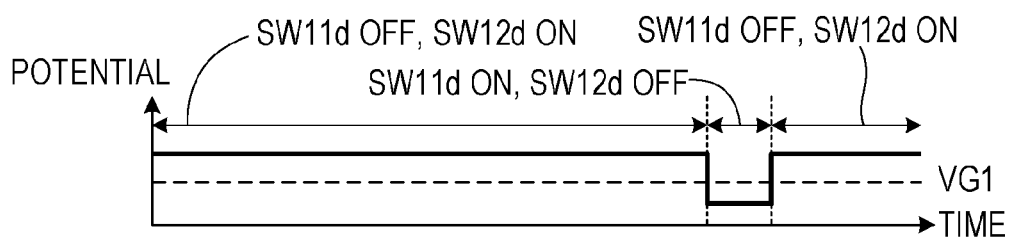

The cathode driving unit 17 includes units for performing switching between a cutoff voltage and an emission voltage to be applied to the cathodes 1a to 1d. As illustrated in FIG. 5, the cathode driving unit 17 includes a cutoff voltage generation unit 19 and an emission voltage generation unit 18 which are connected to cathodes 1a to 1d in common and a selection circuit connected to the cathodes 1a to 1d in an individual manner.

The cutoff voltage generation unit 19 generates a cutoff voltage of DC of 10 V to 200 V using a potential of the extraction electrode 2 as a reference in response to a control signal SG6 supplied from the control circuit unit 14.

Similarly, the emission voltage generation unit 18 generates a cutoff voltage of DC in a range from −10 V to −200 V using the potential of the extraction electrode 2 as a reference in response to a control signal SG5 supplied from the control circuit unit 14.

Cathode voltages are applied to the cathodes 1a to 1d by switching an output from the cutoff voltage generation unit 19 and an output from the emission voltage generation unit 18 from one to another by the selection circuit.

The heater driving unit 20 generates a heater voltage of DC in a range from 5 V to 10 V in response to a control signal supplied from the control circuit unit 14 and applies the heater voltage to the individual heaters 5.

Operation of the selection circuit will be described with reference to FIG. 5 and FIGS. 6A to 6D. The radiation tube 100 includes a plurality of combinations of the cathode 1 and the target 4. However, the plurality of combinations of the cathode 1 and the target 4 do not simultaneously generate radiation, but sequentially generate radiation in a time sharing manner one by one. The selection circuit selects one of the cathodes 1a to 1d so that only the selected one of the cathodes 1a to 1d emits electrons.

The selection circuit includes switches 11a to 11d, switches 12a to 12d, as shown in FIG. 5, and a buffer circuit (not shown).

The switch 11a which performs an on/off operation for connection of an output from the emission voltage generation unit 18 and the switch 12a which performs an on/off operation for connection of an output from the cutoff voltage generation unit 19 are connected to a preceding stage of the cathode 1a in parallel. When electrons are to be emitted from the cathode 1a in accordance with the control signal SG1 supplied from the control circuit unit 14, the switch 11a is turned on and the switch 12a is turned off so that an emission voltage is applied to the cathode 1a. At this time, a cutoff voltage is applied to the other cathodes 1b, 1c, and 1d. In this case, the control signals SG2, SG3, and SG4 cause the switches 11b, 11c, and 11d to be turned off and the switches 12a, 12b, and 12c to be turned on.

Similarly, when electrons are to be emitted from the cathode 1b in accordance with the control signal SG2 supplied from the control circuit unit 14, the switch 11b is turned on and the switch 12b is turned off so that an emission voltage is applied to the cathode 1b. At this time, a cutoff voltage is applied to the other cathodes 1a, 1c, and 1d. In this case, the control signals SG1, SG3, and SG4 cause the switches 11a, 11c, and 11d to be turned off and the switches 12a, 12b, and 12c to be turned on.

The same operations are performed in accordance with the control signals SG3 and SG4, and potentials of the cathodes 1a to 1d are changed at timings illustrated in FIGS. 6A to 6D.

As described above, since the emission voltage is sequentially applied to the cathodes 1a to 1d in a selective manner, radiation is sequentially emitted from the corresponding targets 4.

As the switches, analog switches are employed in this description. However, switching circuits each of which includes a combination of an operation amplifier and a transistor may be used. Furthermore, instead of the switching circuits, electromagnetic relays, photo MOS relays, or mercury relays may be used.

Furthermore, although the four cathodes 1a to 1d are described for simplicity of description, the number of cathodes is not limited to four but 10 to 20 cathodes are preferably used for tomosynthesis photographing.

Second Exemplary Embodiment

A configuration in a second exemplary embodiment is different from that in the first exemplary embodiment only in that a cathode driving unit 17 includes emission voltage generation units 18a to 18d corresponding to cathodes 1a to 1d.

Figure 7:
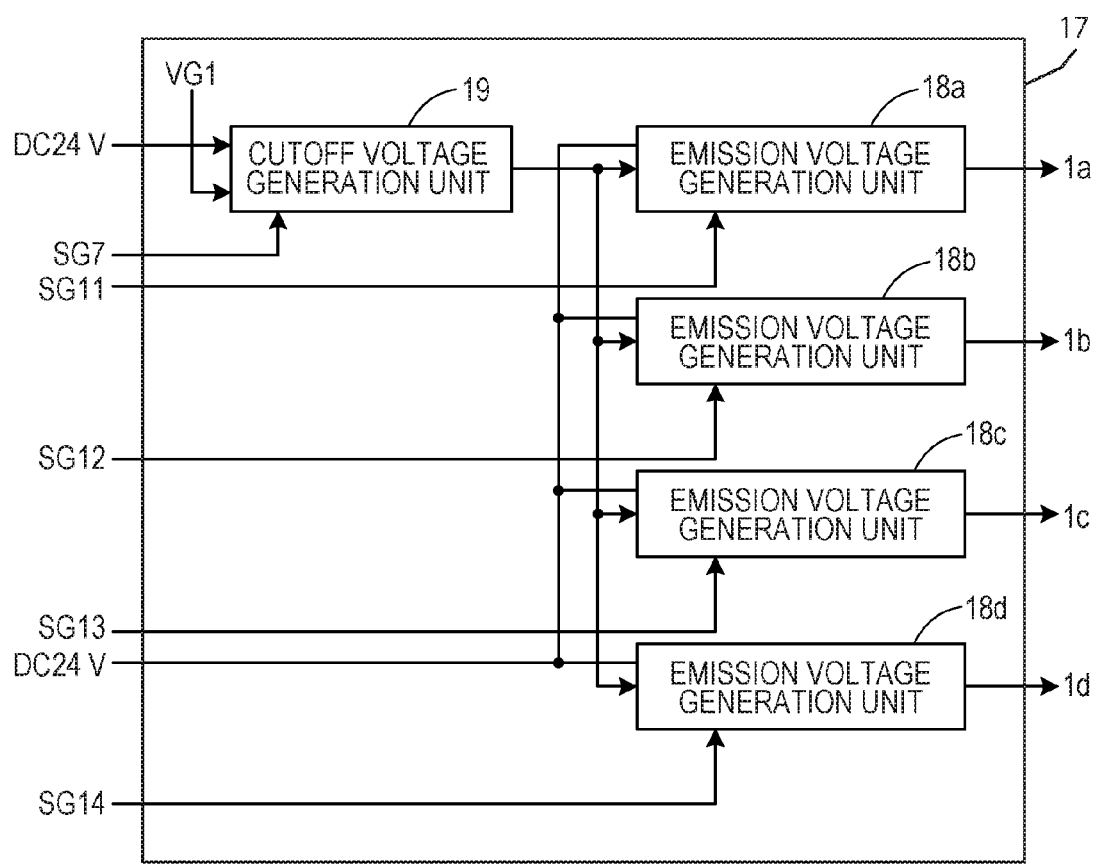
FIG. 7 is a block diagram illustrating a configuration of a cathode driving unit according to a second exemplary embodiment.
Figure 8A:
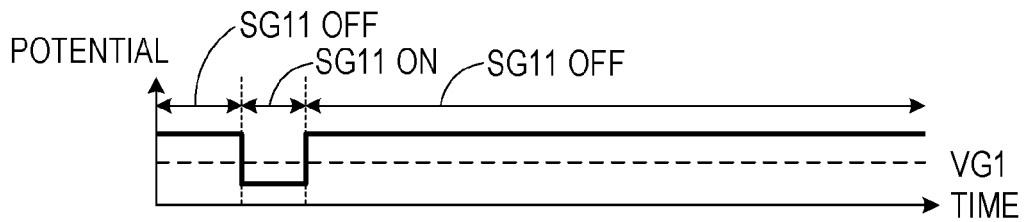
FIGS. 8A, 8B, 8C to 8D are timing charts illustrating timed change of a cathode potential according to the second exemplary embodiment.
Figure 8B:
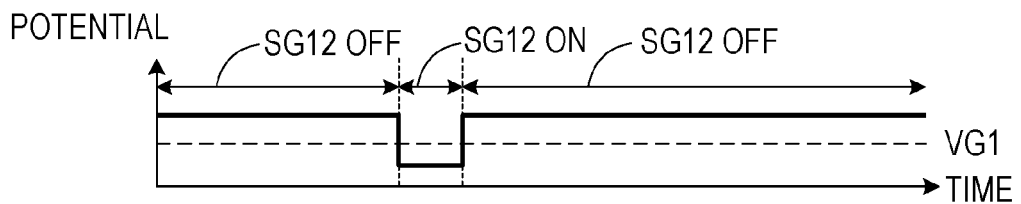
Figure 8C:
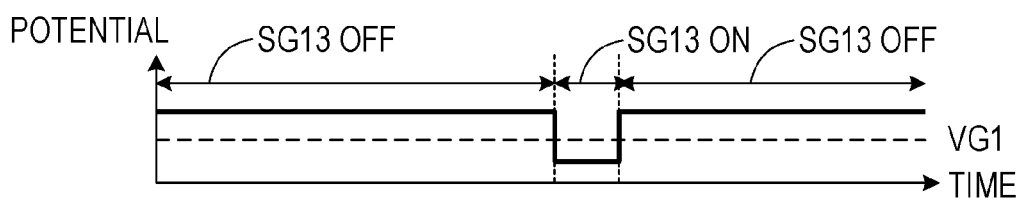
Figure 8D:
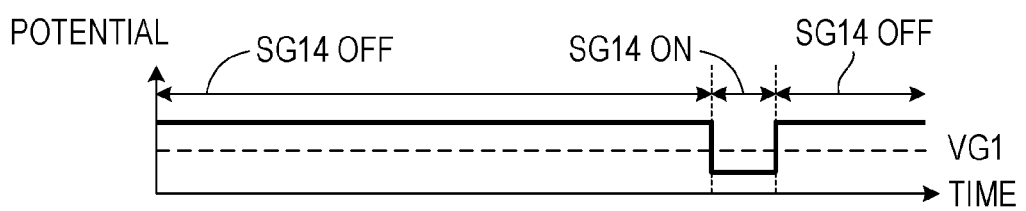

Referring to FIG. 7, operation of the cathode driving unit 17 will be described.

The cathode driving unit 17 includes the emission voltage generation units 18a to 18d connected to the cathodes 1a to 1d, respectively, and a cutoff voltage generation unit 19 connected to the emission voltage generation units 18a to 18d in common. Specifically, cathode voltages to be applied to the cathodes 1a to 1d are generated by overlapping outputs from the emission voltage generation units 18a to 18d on an output of the cutoff voltage generation unit 19.

The cutoff voltage generation unit 19 generates a cutoff voltage of DC in a range from 10 V to 100 V using a potential of an extraction electrode 2 as a reference in response to a control signal SG7 supplied from a control circuit unit 14.

The emission voltage generation unit 18a generates a voltage of DC in a range from −10 V to −300 V in response to a control signal SG11 supplied from the control circuit unit 14, overlaps the voltage on the cutoff voltage, and outputs the resultant voltage as an emission voltage to the cathode 1a. Specifically, the cathode 1a which emits electrons is selected in accordance with an on/off state of the control signal SG11 supplied from the control circuit unit 14. When the control signal SG11 supplied from the control circuit unit 14 is in an off state, the emission voltage generation unit 18a does not generate the emission voltage, and the cutoff voltage is applied to the cathode 1a. When the control signal SG11 supplied from the control circuit unit 14 is in an on state, the emission voltage generation unit 18a generates the emission voltage, and the emission voltage on which the cutoff voltage is overlapped is applied to the cathode 1a.

Similarly, the emission voltage generation unit 18b generates a voltage of DC in a range from −10 V to −300 V in response to a control signal SG12 supplied from the control circuit unit 14, overlaps the voltage on the cutoff voltage, and outputs the resultant voltage as an emission voltage to the cathode 1b. Specifically, when the control signal SG12 supplied from the control circuit unit 14 is in an off state, the emission voltage generation unit 18b does not generate the emission voltage, and the cutoff voltage is applied to the cathode 1b. When the control signal SG12 supplied from the control circuit unit 14 is in an on state, the emission voltage generation unit 18b generates an emission voltage, and the emission voltage on which the cutoff voltage is overlapped is applied to cathode 1b.

The same operations are performed in accordance with control signals SG13 and SG14, and potentials of the cathodes 1a to 1d are changed at timings illustrated in FIGS. 8A to 8D.

Third Exemplary Embodiment

Figure 9:
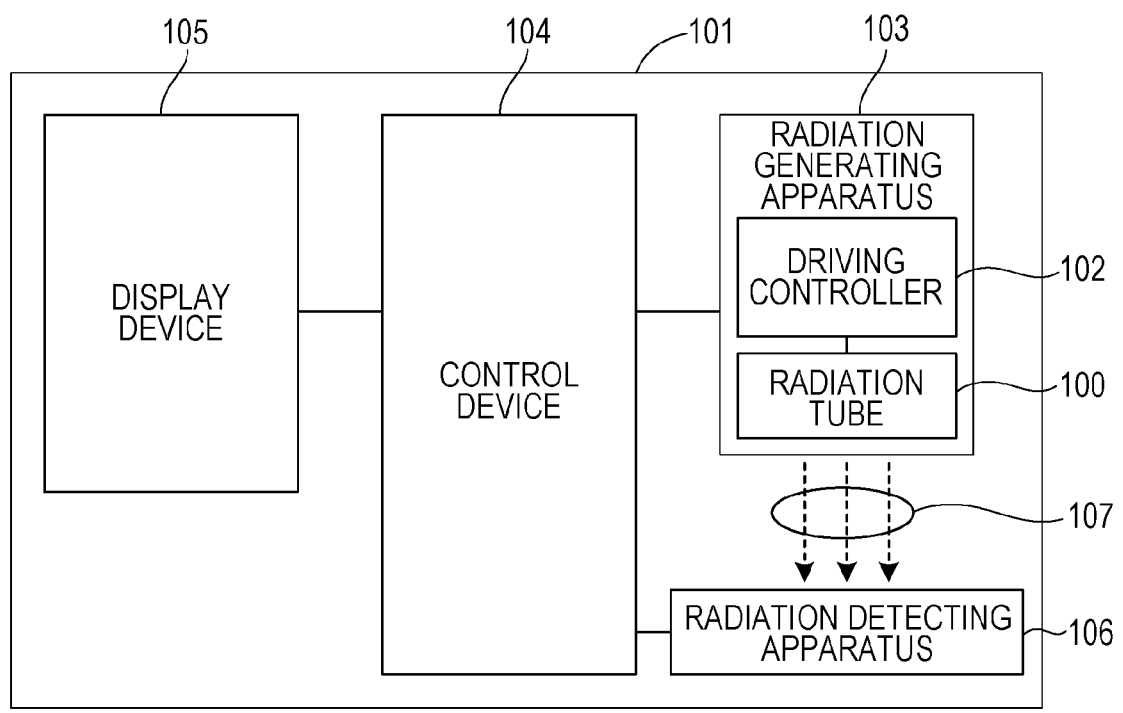
FIG. 9 is a block diagram illustrating a configuration of a radiographic imaging system using a multi-source radiation generating apparatus according to a third exemplary embodiment.

A radiographic imaging system 101 using the radiation generating apparatus 100 according to the first exemplary embodiment or the second exemplary embodiment will be described. FIG. 9 is a block diagram illustrating a configuration of the radiographic imaging system 101 according to a third exemplary embodiment of the present invention.

A control device 104 (e.g., a computer within an imaging modality) controls a radiation generating apparatus 103 (e.g., a multi-source X-ray generator) and a radiation detecting apparatus 106 (e.g., a digital flat panel display) which are operated in combination. The radiation generating apparatus 103 includes a radiation tube 100 and a driving controller 102. The control device 104 outputs various control signals to the radiation tube 100, and a radiation state of radiation irradiated from the radiation generating apparatus 103 is controlled by the control signals. Radiation output from the radiation generating apparatus 103 is transmitted through a subject 107 and is detected by the radiation detecting apparatus 106. The radiation detecting apparatus 106 converts the detected radiation into an image signal and outputs the image signal to the control device 104. The control device 104 outputs a display signal which causes a display device 105 (e.g., a flat screen display LCD) to display an image in accordance with the image signal. The display device 105 displays an image corresponding to the display signal in a screen as a photographed image of the subject.

Although the transmissive radiation generating apparatus has been described in the foregoing exemplary embodiments, the present invention is applicable to a reflective radiation generating apparatus.

The radiation generating apparatus according to the present invention may control emission/non-emission of electrons by selectively switching polarity of a cathode potential relative to an extraction electrode potential while the extraction electrode potential is set constant. According to the present invention, an extraction electrode may be formed as an electrode integrally configured and shared by a plurality of electron sources, and accordingly, a configuration and wiring of the extraction electrode may be simplified. Therefore, a radiation tube may be miniaturized and fabrication cost may be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-153198 filed Jul. 24, 2013, which is hereby incorporated by reference herein in its entirety.

What is claimed is:

1. A radiation generating apparatus comprising:
a radiation tube including a plurality of cathodes, a plurality of targets, and an extraction electrode, the plurality of cathodes being configured to emit electrons, the plurality of targets being disposed in a one-to-one correspondence with the plurality of cathodes and configured to output radiation in response to being irradiated by the electrons, and the extraction electrode being disposed between the plurality of cathodes and the plurality of targets and configured to operate at a potential applied thereto; and
a driving controller configured to control driving of the radiation tube,
wherein the driving controller performs switching between a cutoff potential, which is higher than the potential of the extraction electrode, and an emission potential, which is lower than the potential of the extraction electrode so that the cutoff potential and the emission potential are selectively applied to the plurality of cathodes.

2. The radiation generating apparatus according to claim 1, further comprising:
a voltage source being electrically connected to the plurality of targets and the extraction electrode, and being electrically intervened therebetween; and
a plurality of openings arranged in the extraction electrode,
wherein an arrangement of the plurality of openings corresponds to an arrangement of the plurality of targets and an arrangement of the plurality of cathodes, and
wherein the potential of the extraction electrode is regulated to a certain extraction potential by the voltage source.

3. The radiation generating apparatus according to claim 1, further comprising:
a voltage source being electrically connected to the plurality of targets and the extraction electrode, and being electrically intervened therebetween,
wherein the voltage source applies an acceleration voltage between the plurality of targets and the extraction electrode, such that the potential of the extraction electrode is lower than the potential of the plurality of targets.

4. The radiation generating apparatus according to claim 3, further comprising:
an intermediate electrode disposed between the plurality of targets and the extraction electrode, and
an intermediate electrode potential regulation unit having an intermediate electrode potential source configured to apply an intermediate electrode potential to the intermediate electrode,
wherein the intermediate electrode has a potential higher than the potential of the extraction electrode and lower than the potential of the plurality of targets.

5. The radiation generating apparatus according to claim 1,
wherein the driving controller includes a cutoff voltage generation unit and an emission voltage generation unit which are disposed for the plurality of cathodes in common, and
wherein the driving controller further includes switches arranged for each of the plurality of cathodes which perform switching between the cutoff potential supplied from the cutoff voltage generation unit and the emission potential supplied from the emission voltage generation unit.

6. The radiation generating apparatus according to claim 1,
wherein the driving controller includes a cutoff voltage generation unit disposed for the plurality of cathodes in common and a plurality of emission voltage generation units corresponding to the plurality of cathodes, and
wherein the plurality of emission voltage generation units selectively overlap emission voltages on a cutoff potential to be applied to the plurality of cathodes from the cutoff voltage generation unit.

7. The radiation generating apparatus according to claim 1,
wherein the radiation tube includes a vacuum container which encloses the plurality of cathodes and the extraction electrode thereinside.

8. A radiographic imaging system comprising:
the radiation generating apparatus set forth in claim 1;
a radiation detecting apparatus configured to detect radiation which is emitted from the radiation generating apparatus and which is transmitted through a subject; and
a control device configured to control the radiation generating apparatus and the radiation detecting apparatus in combination.

* * * * *